United States Patent
Miwa et al.

(10) Patent No.: US 12,274,504 B2
(45) Date of Patent: Apr. 15, 2025

(54) NON-CONTACT ULTRASONIC OPHTHALMOTONOMETER

(71) Applicant: NIDEK CO., LTD., Aichi (JP)

(72) Inventors: Tetsuyuki Miwa, Aichi (JP); Kazunari Shimizu, Aichi (JP); Shirohisa Kobayashi, Aichi (JP); Tsutomu Uemura, Aichi (JP); Kenji Nakamura, Aichi (JP)

(73) Assignee: NIDEK CO., LTD., Aichi (JP)

( * ) Notice: Subject to any disclaimer, the term of this patent is extended or adjusted under 35 U.S.C. 154(b) by 1101 days.

(21) Appl. No.: 17/043,317

(22) PCT Filed: Mar. 26, 2019

(86) PCT No.: PCT/JP2019/013032
§ 371 (c)(1),
(2) Date: Nov. 13, 2020

(87) PCT Pub. No.: WO2019/189272
PCT Pub. Date: Oct. 3, 2019

(65) Prior Publication Data
US 2021/0068656 A1    Mar. 11, 2021

(30) Foreign Application Priority Data

Mar. 30, 2018  (JP) .................................. 2018-068717
Mar. 30, 2018  (JP) .................................. 2018-068718

(51) Int. Cl.
*A61B 3/16*  (2006.01)
*A61B 5/00*  (2006.01)

(52) U.S. Cl.
CPC .......... *A61B 3/165* (2013.01); *A61B 2560/04* (2013.01)

(58) Field of Classification Search
CPC ............. A61B 3/16; A61B 3/165; A61B 8/10; A61B 2560/04
See application file for complete search history.

(56) References Cited

U.S. PATENT DOCUMENTS

| | | | |
|---|---|---|---|
| 3,948,248 A * | 4/1976 | Zuckerman | A61B 8/10 600/463 |
| 5,180,363 A * | 1/1993 | Idemoto | B06B 1/0253 606/171 |
| 5,636,635 A | 6/1997 | Massie et al. | |
| 10,842,672 B2 * | 11/2020 | Citterio | A61F 9/007 |

(Continued)

FOREIGN PATENT DOCUMENTS

| | | | |
|---|---|---|---|
| JP | 60-227729 A | 11/1985 | |
| JP | 01242047 A * | 9/1989 | ............... A61B 8/10 |

(Continued)

OTHER PUBLICATIONS

STIC search results (Year: 2024).*

(Continued)

*Primary Examiner* — May A Abouelela
(74) *Attorney, Agent, or Firm* — RANKIN, HILL & CLARK LLP

(57) ABSTRACT

A non-contact ultrasonic tonometer for measuring the eye pressure of an examinee's eye by use of ultrasound includes a Langevin transducer. The Langevin transducer applies ultrasound to the examinee's eye to measure the eye pressure of the examinee's eye. Further, A non-contact ultrasonic tonometer for measuring the eye pressure of an examinee's eye by use of ultrasound includes: ultrasonic generating means for generating ultrasound; a support base supporting the ultrasonic generating means; and attaching means for attaching the ultrasonic generating means to the support base.

18 Claims, 7 Drawing Sheets

(56) References Cited

U.S. PATENT DOCUMENTS

| | | | |
|---|---|---|---|
| 2007/0197893 A1 | 8/2007 | Nakai et al. | |
| 2009/0069712 A1* | 3/2009 | Mulvihill | A61B 17/3415 600/564 |
| 2009/0069830 A1* | 3/2009 | Mulvihill | A61B 17/320068 606/171 |
| 2009/0275819 A1* | 11/2009 | Miwa | A61B 8/10 600/399 |
| 2010/0069737 A1 | 3/2010 | Jinde et al. | |
| 2010/0312087 A1* | 12/2010 | Miwa | A61B 3/152 600/400 |
| 2010/0324406 A1* | 12/2010 | Miwa | A61B 3/165 600/400 |
| 2012/0190961 A1* | 7/2012 | Luce | A61B 3/165 600/401 |
| 2012/0209303 A1* | 8/2012 | Frankhouser | A61B 17/3476 606/169 |
| 2017/0280998 A1* | 10/2017 | Ariga | A61B 3/165 |

FOREIGN PATENT DOCUMENTS

| | | |
|---|---|---|
| JP | 5-253190 A | 10/1993 |
| JP | 2005-304930 A | 11/2005 |
| JP | 2009-268651 A | 11/2009 |
| JP | 2010-68874 A | 4/2010 |
| JP | 2015-92980 A | 5/2015 |
| WO | WO-2016122772 A1 * | 8/2016 ............... A61B 3/16 |

OTHER PUBLICATIONS

International Search Report (ISR) dated May 28, 2019 filed in PCT/JP2019/013032.

Ultrasonic Handbook, Aug. 30, 1999, pp. 662 & 663, Maruzen Co., Ltd. and its non-official English translation, total 7 pages.; Cited in International Search Report dated May 28, 2019 filed in PCT/JP2019/013032.

* cited by examiner

NON-CONTACT ULTRASONIC OPHTHALMOTONOMETER

TECHNICAL FIELD

The present disclosure relates to a non-contact ultrasonic tonometer that measures the eye pressure of an examinee's eye by use of ultrasound.

BACKGROUND ART

An air-puff tonometer is still common as a non-contact tonometer. The air-puff tonometer detects the applanated state of the cornea at the time of puffing air onto the cornea, and air pressure puffed onto the cornea and, accordingly, converts the air pressure in the predetermined deformed state into eye pressure.

Moreover, an ultrasonic tonometer that measures eye pressure by use of ultrasound has been proposed as a non-contact tonometer (refer to Patent Literature 1). The ultrasonic tonometer of Patent Literature 1 detects the applanated state of the cornea at the time of radiating ultrasound on the cornea, and the radiation pressure exerted on the cornea and, accordingly, converts the radiation pressure in the predetermined deformed state into eye pressure.

Moreover, an apparatus that measures eye pressure on the basis of the relationship between the properties (amplitude and phase) of a reflected wave from the cornea and the eye pressure has been proposed as an ultrasonic tonometer (refer to Patent Literature 2).

Moreover, an apparatus using a broadband air-coupled ultrasonic probe that transmits and receives an ultrasonic beam with a broadband frequency component in an ultrasonic tonometer has been proposed (refer to Patent Literature 3).

CITATION LIST

Patent Literature

PATENT LITERATURE 1: JP-A-05-253190
PATENT LITERATURE 2: JP-A-2009-268651
PATENT LITERATURE 3: JP-A-2010-068874

SUMMARY OF INVENTION

However, the known apparatuses cannot appropriately apply ultrasound to the cornea of an examinee's eye. For example, the apparatus of Patent Literature 1 cannot appropriately apply ultrasound to the cornea and cannot actually apply, to the examinee's eye, ultrasound at a level that flattens or indents the cornea. Moreover, for example, the apparatus of Patent Literature 2 cannot appropriately apply ultrasound to the cornea and cannot detect the properties of a reflected wave satisfactorily. Moreover, even if, for example, the broadband air-coupled ultrasonic probe of Patent Literature 3 is used, it is not possible to obtain sufficient ultrasound output in reality.

The present disclosure has been made considering the known problems. A technical issue of the present disclosure is to provide a non-contact ultrasonic tonometer that can appropriately apply ultrasound to an examinee's eye.

In order to solve the above issue, the present disclosure is characterized by the following configurations:

(1) A non-contact ultrasonic tonometer for measuring the eye pressure of an examinee's eye by use of ultrasound, including a Langevin transducer. The Langevin transducer applies ultrasound to the examinee's eye to measure the eye pressure of the examinee's eye.

(2) A non-contact ultrasonic tonometer for measuring the eye pressure of an examinee's eye by use of ultrasound, including: ultrasonic generating means for generating ultrasound; a support base supporting the ultrasonic generating means; and attaching means for attaching the ultrasonic generating means to the support base.

DESCRIPTION OF EMBODIMENTS

First Embodiment

Figure 1:
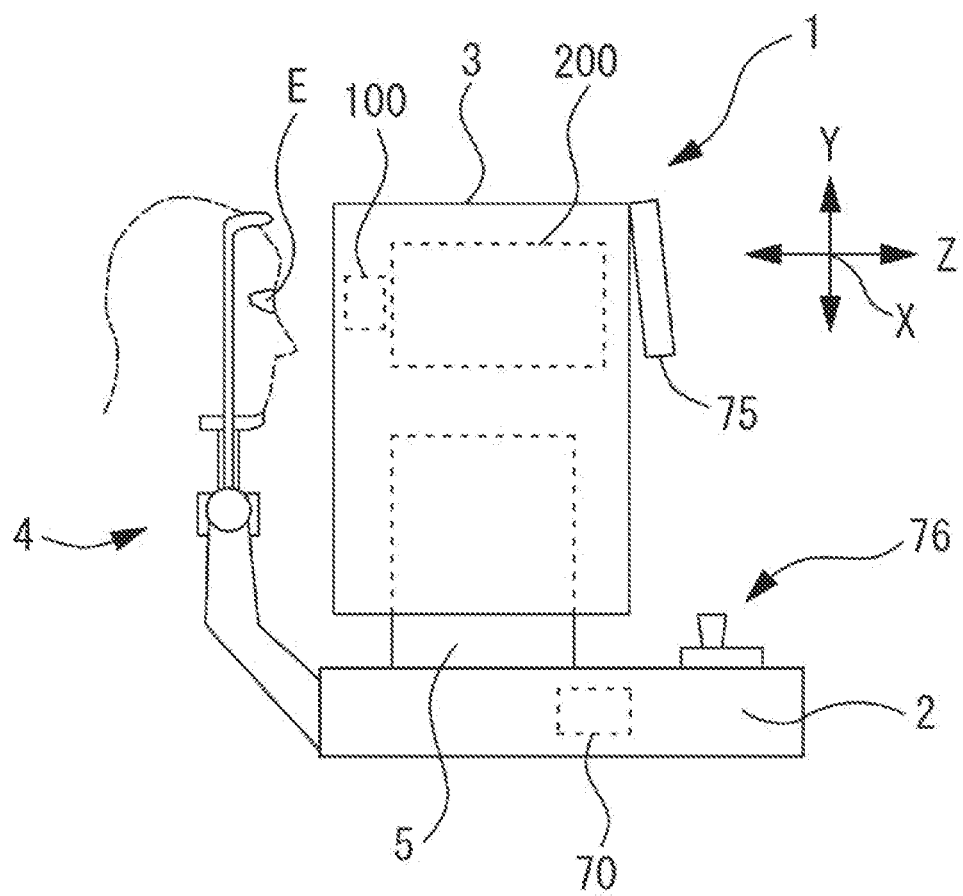
FIG. 1 is an external view of a non-contact ultrasonic tonometer of the example.

A first embodiment according to the present disclosure is described below. A non-contact ultrasonic tonometer (for example, a non-contact ultrasonic tonometer 1) of the first embodiment uses ultrasound to measure the eye pressure of an examinee's eye. The non-contact ultrasonic tonometer includes, for example, an ultrasonic generator (for example, an ultrasonic unit 100). The ultrasonic generator generates, for example, ultrasound. The ultrasonic generator is, for example, a Langevin transducer. The Langevin transducer includes, a sonotrode (also referred to as a horn or front mass), a back mass (for example, a back mass 132), and an ultrasonic element (for example, an ultrasonic element 110). The sonotrode (for example, a sonotrode 131) or the back mass is a mass member made of, for example, metal. The ultrasonic element is, for example, a piezoelectric element or magnetostrictor. The ultrasonic element is sandwiched between the sonotrode and the back mass.

The non-contact ultrasonic tonometer of the first embodiment uses the Langevin transducer and, accordingly, can measure eye pressure while fully deforming an examinee's eye under acoustic radiation pressure.

The ultrasonic generator may include a plurality of ultrasonic elements. In this case, ultrasound may be generated by a resonance phenomenon caused by the plurality of ultrasonic elements. The plurality of ultrasonic elements is resonated; accordingly, a high-power ultrasound can be generated.

The Langevin transducer may be hollow. For example, the Langevin transducer may be cylindrical and include an opening (for example, an opening 101). In this case, an optical axis of an optical system (for example, an optical unit 200) such as a measuring optical system or observing optical system may be placed in the opening of the Langevin transducer. For example, the optical system projects light onto the examinee's eye, or receives light from the examinee's eye, through the opening of the Langevin transducer. In this manner, the optical axis of the optical system is placed in the opening of the Langevin transducer; accordingly, it is possible to easily and optically measure or observe the examinee's eye.

The apparatus may further include a fastening member (for example, a fastening member 160). For example, the sonotrode and the back mass are clamped with the fastening member in their respective directions. The fastening member may be, for example, a bolt or hollow bolt. In this case, female threads (for example, female threads 133 and 134) are formed in the sonotrode and the back mass. Moreover, the fastening member may be a vise, clip, or the like. A hollow bolt is used as the fastening member to allow placing the optical axis of the measuring or observing optical system in the opening. Consequently, the sonotrode and the back mass are clamped together, and it is easy to perform a measurement or observation with the optical system. For example, it is easy to perform a measurement or observation with the optical system in a direction of a beam axis of the Langevin transducer.

The non-contact ultrasonic tonometer may further include a controller (for example, a controller 70). The controller may calculate the eye pressure of the examinee's eye on the basis of output information of the ultrasonic generator. For example, the output information may be, for example, the acoustic radiation pressure, irradiation time (for example, time elapsed from the input of a trigger signal), or frequency of ultrasound.

Moreover, for example, a deformation detector (for example, a deformation detecting system 260) that detects the deformation of the cornea may be provided. In this case, the controller calculates the eye pressure of the examinee's eye on the basis of a detection result of the deformation detector. For example, the eye pressure may be calculated on the basis of the output information of ultrasound of when the ultrasound makes the cornea deformed into a predetermined shape.

Second Embodiment

A second embodiment according to the present disclosure is described below. A non-contact ultrasonic tonometer (for example, a non-contact ultrasonic tonometer 1) of the second embodiment measures the eye pressure of an examinee's eye, for example, by use of ultrasound. The non-contact ultrasonic tonometer mainly includes, for example, an ultrasonic generator (for example, an ultrasonic unit 100), a support base (for example, a support base 6), and an attachment (an attachment 400). For example, the ultrasonic generator generates ultrasound, and applies the ultrasound to the examinee's eye. For example, the support base supports the ultrasonic generator. The attachment attaches the ultrasonic generator to the support base in such a manner as not to influence ultrasound that is applied to the examinee's eye. Examples of the influence on ultrasound include a reduction in the sound pressure of ultrasound, and a disturbance to the convergence of an ultrasonic beam. The ultrasonic generator is attached to the support base in such a manner as not to have an adverse effect on ultrasound that is applied to the examinee's eye; accordingly, the non-contact tonometer of the second embodiment can apply sufficient power ultrasound to the examinee's eye.

The attachment may hold the ultrasonic generator via a vibration-isolating member (for example, a first vibration-isolating member 421 and a second vibration-isolating member 422). Consequently, it is possible to prevent ultrasound vibrations from propagating around the ultrasonic generator. The vibration-isolating member may be, for example, a rubber isolator such as ethylene propylene rubber, or other resins such as a gel isolator. A grease isolator may be applied as the vibration-isolating member to the attachment.

The ultrasonic generator may be a Langevin transducer. The Langevin transducer may include, for example, a sonotrode (for example, a sonotrode 131), a back mass (for example, a back mass 132), and an ultrasonic element (for example, an ultrasonic element 110) placed between the sonotrode and the back mass. In this case, the attachment may hold the back mass. Holding the back mass makes it possible to suppress influence on ultrasound as compared to a case of holding the sonotrode. Therefore, the attachment can hold the ultrasonic generator without contacting the sonotrode. Consequently, for example, the non-contact tonometer of the second embodiment can attach the ultrasonic generator to the support base in such a manner as to prevent a reduction in ultrasound output due to contact of, for example, the support base with the sonotrode that propagates ultrasound through the air.

The back mass may include a flange (for example, a flange 135). In this case, the attachment may hold the flange. The flange may have, for example, a disc shape, a rectangular shape, or an arbitrary shape. The flange is simply required to have a shape that is easy for the attachment to hold. The flange may be configured integrally with, or configured of a different member from, the back mass. For example, the attachment may hold the flange mounted on the back mass. The attachment may hold the back mass or flange as a result of the back mass or flange gripping the attachment. For example, the attachment substantially holds the back mass.

The Langevin transducer may include a fastening member (for example, a fastening member 160). The sonotrode and the back mass are clamped with the fastening member in a direction pulling each other. The fastening member is, for example, a bolt or hollow bolt. In this case, the attachment may hold the fastening member. Holding the fastening member can suppress influence on ultrasound as compared to a case of holding the sonotrode.

The support base may include, for example, an opening (for example, an opening 6a) larger than the diameter of the sonotrode. In this case, it is possible to prevent the support base from contacting the sonotrode, for example, even if the sonotrode is inserted through the opening.

Example

An example according to the present disclosure is described below. A non-contact ultrasonic tonometer of the example uses, for example, ultrasound to measure the eye pressure of an examinee's eye in a non-contact manner.

FIG. 1 illustrates the external appearance of the apparatus. An ultrasonic tonometer 1 includes, for example, a base 2, a measuring device 3, a face supporter 4, and a driver 5. The measuring device 3 is described below. The face supporter 4 supports the face of the examinee's eye. The face supporter 4 is installed, for example, on the base 2. The driver 5 moves the measuring device 3 with respect to the base 2, for example, for alignment.

Figure 2:
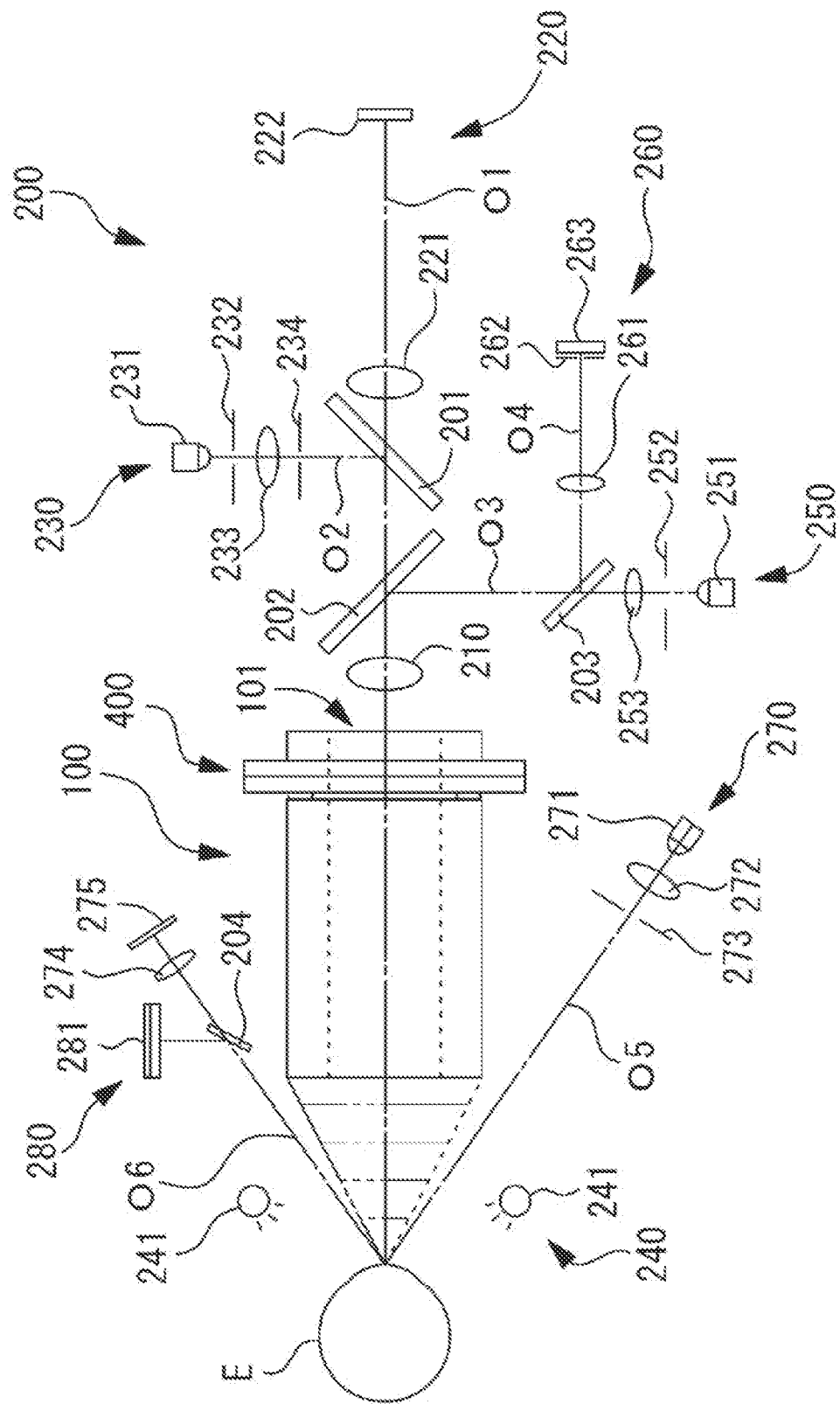
FIG. 2 is a schematic diagram illustrating an optical system of the example.

FIG. 2 is a schematic diagram of the main configuration of the measuring device 3. The measuring device 3 performs, for example, a measurement and an observation on the examinee's eye. The measuring device 3 includes, for example, an ultrasonic unit 100 and an optical unit 200. The ultrasonic unit 100 and the optical unit 200 are described in turn, using FIG. 2.

For example, the ultrasonic unit 100 applies ultrasound to an examinee's eye E. For example, the ultrasonic unit 100 applies ultrasound to the cornea to generate acoustic radiation pressure on the cornea. Acoustic radiation pressure is, for example, the force exerted in a travel direction of a sound wave. The ultrasonic tonometer 1 of the example deforms the cornea by use of, for example, the acoustic radiation pressure. The ultrasonic unit of the example is cylindrical, and includes, in the center, an opening 101 where an optical axis O1 of the optical unit 200 described below is placed.

Figure 3A:
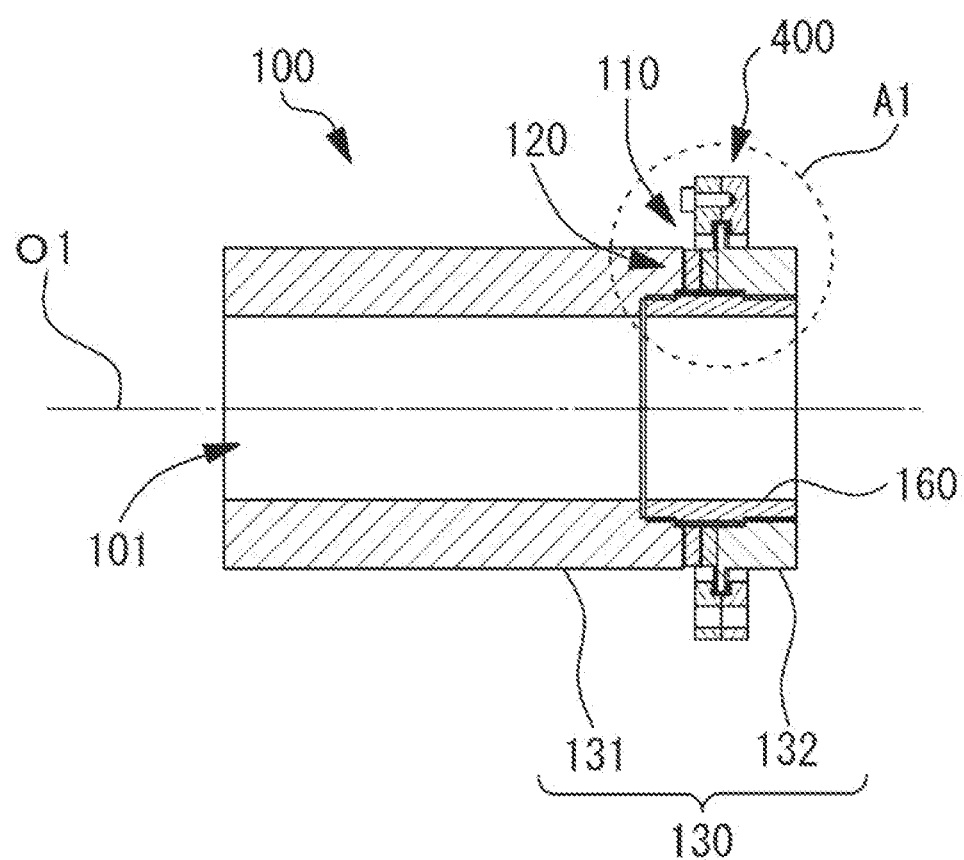
FIG. 3A is a schematic cross-sectional view of an ultrasonic unit.
Figure 3B:
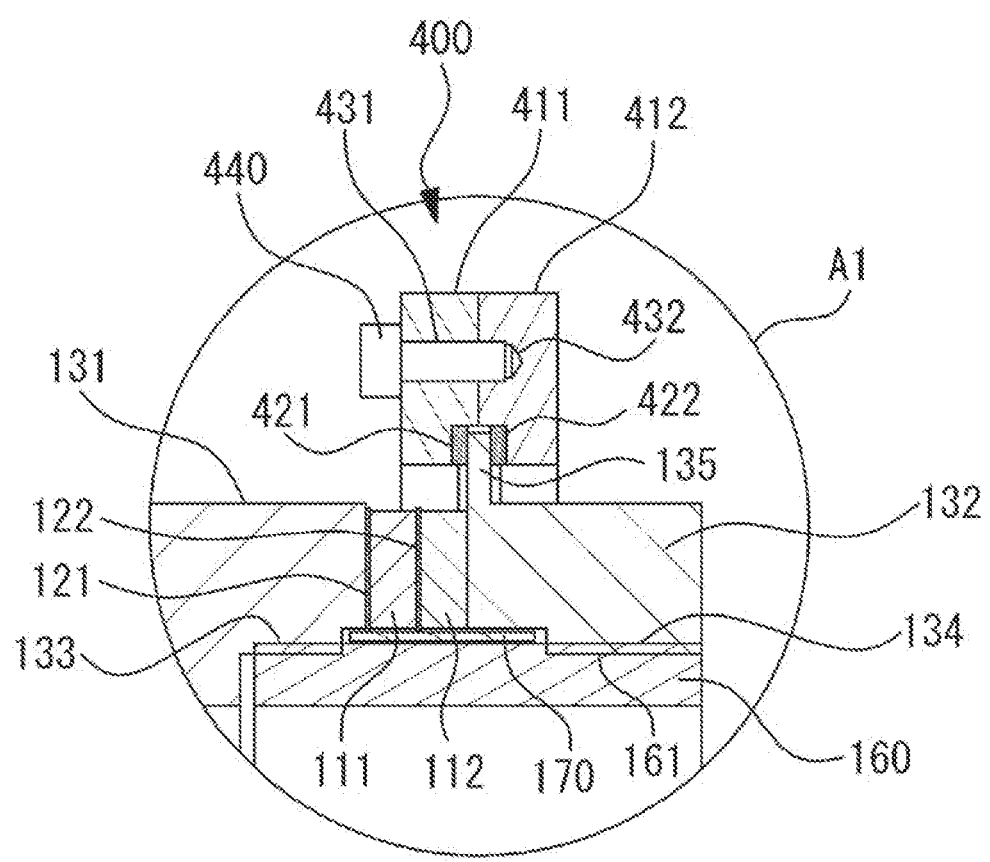
FIG. 3B is a schematic cross-sectional view of the ultrasonic unit.

FIG. 3A is a cross-sectional view illustrating the schematic configuration of the ultrasonic unit 100. FIG. 3B is a state where an area A1 illustrated in FIG. 3A is enlarged. The ultrasonic unit 100 of the example is what is called a Langevin transducer. The ultrasonic unit 100 includes, for example, an ultrasonic element 110, an electrode 120, a mass member 130, and a fastening member 160. The ultrasonic element 110 generates ultrasound. The ultrasonic element 110 may be a voltage element (for example, a piezoelectric ceramic) or magnetostrictor. The ultrasonic element 110 of the example has a ring shape. For example, the ultrasonic element 110 may be a device where a plurality of piezoelectric elements is stacked. In the example, two stacked piezoelectric elements (for example, a piezoelectric element 111 and a piezoelectric element 112) are used for the ultrasonic element 110. For example, the two piezoelectric elements are connected to the electrode 120 (an electrode 121 and an electrode 122), respectively. The electrodes 121 and 122 of the example have, for example, a ring shape.

The mass member 130 sandwiches, for example, the ultrasonic element 110. The mass member 130 sandwiches the ultrasonic element 110, accordingly, the tensile strength of the ultrasonic element 110 is increased, for example, to be rendered resistant to strong vibration. Consequently, it is possible to generate high-power ultrasound. The mass member 130 may be, for example, a metal block. The mass member 130 includes, for example, a sonotrode (also referred to as a horn or front mass) 131 and a back mass 132.

The sonotrode 131 is a mass member placed ahead of the ultrasonic element 110 (on the examinee's eye side). The sonotrode 131 propagates the ultrasound generated by the ultrasonic element 110 through the air. The sonotrode 131 of the example is cylindrical. A female thread 133 is formed on a part of an inner circle of the sonotrode 131. The female thread 133 is threadedly engaged with a male thread 161 formed on the fastening member 160 described below. The sonotrode 131 may have a shape that causes ultrasound to converge. For example, an end surface on the examinee's eye side of the sonotrode 131 may be inclined toward the opening 101 and have a tapered shape. Moreover, the sonotrode 131 may be a cylinder having an uneven thickness. For example, the sonotrode 131 may have a shape where the outer diameter and the inner dimeter change in the longitudinal direction of the cylinder.

The back mass 132 is a mass member placed behind the ultrasonic element 110. The back mass 132, together with the sonotrode 131, sandwiches the ultrasonic element 110. The back mass 132 is, for example, cylindrical. A female thread 134 is formed on a part of an inner circle of the back mass 132. The female thread 134 is threadedly engaged with the male thread 161 of the fastening member 160 described below. Moreover, the back mass 132 includes a flange 135. The flange 135 is held by an attachment 400 described below.

For example, the mass member 130 and the ultrasonic element 110 sandwiched by the mass member 130 are clamped with the fastening member 160. The fastening member 160 is, for example, a hollow bolt. The fastening member 160 is, for example, cylindrical and includes the male thread 161 on an outer circle thereof. The male thread 161 of the fastening member 160 is threadedly engaged with the female threads 133 and 134 formed on the inner sides of the sonotrode 131 and the back mass 132. The sonotrode 131 and the back mass 132 are clamped with the fastening member 160 in a direction pulling each other. Consequently, the ultrasonic element 110 sandwiched between the sonotrode 131 and the back mass 132 is clamped, and pressure is applied to the ultrasonic element 110.

The ultrasonic unit 100 may include an insulating member 170. The insulating member 170 prevents, for example, the electrode 120 and the ultrasonic element 110 from contacting the fastening member 160. The insulating member 170 is placed, for example, between the electrode 120 and the fastening member 160. The insulating member 170 has, for example, a sleeve shape.

Optical Unit

The optical unit 200 performs, for example, an observation or measurement on the examinee's eye (refer to FIG. 2). The optical unit 200 includes, for example, an objective system 210, an observing system 220, a fixation target projecting system 230, a target projecting system 250, a deformation detecting system 260, a dichroic mirror 201, a beam splitter 202, a beam splitter 203, and a beam splitter 204.

The objective system 210 is, for example, an optical system for taking light from the outside of the measuring device 3 into the optical unit 200, or applying light from the optical unit 200 to the outside of the measuring device 3. The objective lens 210 includes, for example, an optical device. The objective system 210 may include an optical device (for example, an objective lens or relay lens).

An illuminating optical system 240 illuminates the examinee's eye. The illuminating optical system 240 illuminates the examinee's eye with, for example, infrared light. The illuminating optical system 240 includes, for example, an illuminating light source 241. The illuminating light source 241 is placed, for example, obliquely in front of the examinee's eye. The illuminating light source 241 emits, for example, infrared light. The illuminating optical system 240 may include, a plurality of the illuminating light sources 241.

The observing system 220 takes, for example, an observation image of the examinee's eye. The observing system 220 takes, for example, an anterior segment image of the examinee's eye. The observing system 220 includes, for example, a light receiving lens 221 and a photo detector 222. The observing system 220 receives, for example, the light of the illuminating light source 241 reflected from the examinee's eye. The observing system receives, for example, a reflected light flux from the examinee's eye with the optical axis O1 as the center. For example, the reflected light from the examinee's eye passes through the opening 110 of the ultrasonic unit 100, and is received by the photo detector 222 via the objective system 210 and the light receiving lens 221.

The fixation target projecting system 230 projects, for example, a fixation target to the examinee's eye. The fixation target projecting system 230 includes, for example, a target light source 231, a diaphragm 232, a light projecting lens 233, and a diaphragm 234. Light from the target light source 231 passes through, for example, the diaphragm 232, the light projecting lens 233, and the diaphragm 232 along an optical axis O2, and is reflected by the dichroic mirror 201. For example, the dichroic mirror 201 renders the optical axis O2 of the fixation target projecting system 230 coaxial with the optical axis O1. The light of the target light source 231 reflected by the dichroic mirror 201 passes through the objective system 210 along the optical axis O1, and is applied to the examinee's eye. The examinee fixates the target of the fixation target projecting system 230, which stabilize the visual line of the examinee.

The target projecting system 250 projects, for example, a target onto the examinee's eye. The target projecting system 250 projects a target for XY alignment onto the examinee's eye. The target projecting system 250 includes, for example, a target light source (may be, for example, an infrared light source) 251, a diaphragm 252, and a light projecting lens 253. Light from the target light source 251 passes through the diaphragm 252 and the light projecting lens 253 along an optical axis O3, and is reflected by the beam splitter 202. For example, the beam splitter 202 renders the optical axis O3 of the target projecting system 250 coaxial with the optical axis O1. The light of the target light source 251 reflected by the beam splitter 202 passes through the objective system 210 along the optical axis O1, and is applied to the examinee's eye. The light of the target light source 251 applied to the examinee's eye is reflected by the examinee's eye, passes again through, for example, the objective system 210 and the light receiving lens 221 along the optical axis O1, and is received by the photo detector 222. The target received by the photo detector is used for, for example, XY alignment. In this case, for example, the target projecting system 250 and the observing system 220 function as XY alignment detection means.

The deformation detecting system 260 detects, for example, the corneal shape of the examinee's eye. The deformation detecting system 260 detects, for example, the deformation of the cornea of the examinee's eye. The deformation detecting system 260 includes, for example, a light receiving lens 261, a diaphragm 262, and a photo detector 263. The deformation detecting system 260 may detect the deformation of the cornea, for example, on the basis of cornea reflected light received by the photo detector 263. For example, the deformation detecting system 260 may detect the deformation of the cornea by causing the photo detector 263 to receive the light of the target light source 251 reflected from the cornea of the examinee's eye. For example, the cornea reflected light passes through the objective system 210 along the optical axis O1, and is reflected by the beam splitters 202 and 203. The cornea reflected light passes through the light receiving lens 261 and the diaphragm 262 along an optical axis O4, and is received by the photo detector 263.

The deformation detecting system 260 may detect the deformed state of the cornea, for example, on the basis of the magnitude of a light receiving signal of the photo detector 236. For example, the deformation detecting system 260 may detect that the cornea has entered an applanated state when the amount of light received by the photo detector 236 is at its maximum. In this case, for example, the deformation detecting system 260 is set in such a manner that when the cornea of the examinee's eye is in the applanated state, the amount of light received is at the maximum.

The deformation detecting system 260 may be an anterior segment tomographic image imaging unit such as OCT equipment or a Scheimpflug camera. The deformation detecting system 260 may detect, for example, the deformation amount, deformation speed, or the like of the cornea.

A corneal thickness measuring system 270 measures, for example, the corneal thickness of the examinee's eye. The corneal thickness measuring system 270 may include, for example, a light source 271, a light projecting lens 272, a diaphragm 273, a light receiving lens 274, and a photo detector 275. For example, light from the light source 271 passes through the light projecting lens 272 and the diaphragm 273 along an optical axis O5, and is applied to the examinee's eye. Reflected light reflected from the examinee's eye is condensed by the light receiving lens 274 along an optical axis O6 and received by the photo detector 275.

A Z alignment detecting system 280 detects, for example, an alignment state in the Z direction. The Z alignment detecting system 280 includes, for example, a photo detector 281. For example, the Z alignment detecting system 280 may detect the alignment state in the Z direction by detecting the reflected light from the cornea. For example, the Z alignment detecting system may receive reflected light being the light of the light source 271 reflected from the cornea of the examinee's eye. In this case, the Z alignment detecting system 280 may receive, for example, a bright spot created by the cornea of the examinee's eye reflecting the light of the light source 271. In this manner, the light source 271 may also be used as a light source for detecting Z alignment. For example, the light of the light source 271 reflected from the cornea is reflected by the beam splitter 204 along the optical axis O6 and received by the photo detector 281.

Attachment

The attachment 400 attaches the ultrasonic unit 100 to a support base 6 described below in such a manner as not to influence the ultrasound emitted by the ultrasonic unit 100. As illustrated in FIGS. 3A and 3B, the attachment 400 includes, for example, a first flange 411, a second flange 412, a first vibration-isolating member 421, a second vibration-isolating member 422, and a bolt 440. The attachment 400 holds, for example, the flange 135 of the back mass 132. For example, the attachment 400 holds the flange 135 of the back mass 132 by the first flange 411 and the second flange 412. At this point in time, the attachment 400 holds the flange 135 via the first vibration-isolating member 421 and the second vibration-isolating member 422. In other words, the first vibration-isolating member 421 is placed between the first flange 411 and the flange 135, and the second vibration-isolating member 422 is placed between the second flange 412 and the flange 135. Consequently, direct contact of the first flange 411 and the second flange 412 with the back mass 132 is avoided. The first vibration-isolating member 421 and the second vibration-isolating member 422 may be, for example, elastic bodies such as rubber. Moreover, a grease isolator may be applied to the first flange 411, the second flange 412, the first vibration-isolating member 421, the second vibration-isolating member 422, and the like. The bolt 440 is threadedly engaged with a female thread 432 formed in the second flange 412, through a through-hole 431 formed in the first flange 411. Consequently, the first flange 411 and the second flange 412 are clamped in a direction pulling each other. This force allows the attachment 400 to hold the flange 135 of the back mass 132.

Figure 4:
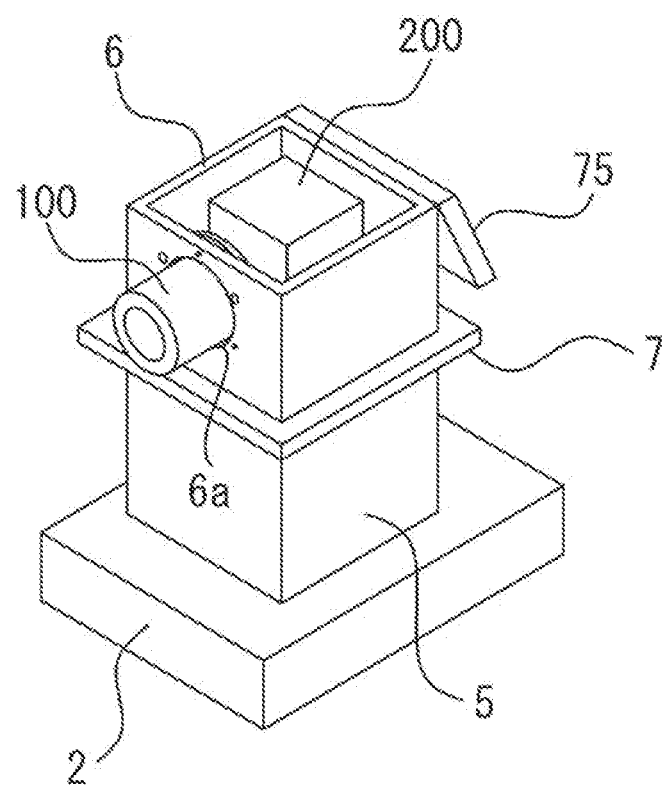
FIG. 4 is a schematic diagram illustrating the interior of a measuring device.

When the ultrasonic unit 100 is attached to the support base 6, the attachment 400 holding the ultrasonic unit 100 is attached to the support base 6. As illustrated in FIG. 4, the support base 6 is provided, for example, on a moving base 7 that is moved by the driver 5. The support base 6 is provided with, for example, an opening 6a for threading the sonotrode 131 therethrough. In the example of FIG. 4, the support base 6 has a box shape. The support base 6 may have any shape as long as it can support the ultrasonic unit 100. Naturally, the support base 6 may be provided integrally with a cover of the measuring device 3, integrally with the optical unit 200, or integrally with other configurations.

Figure 5A:
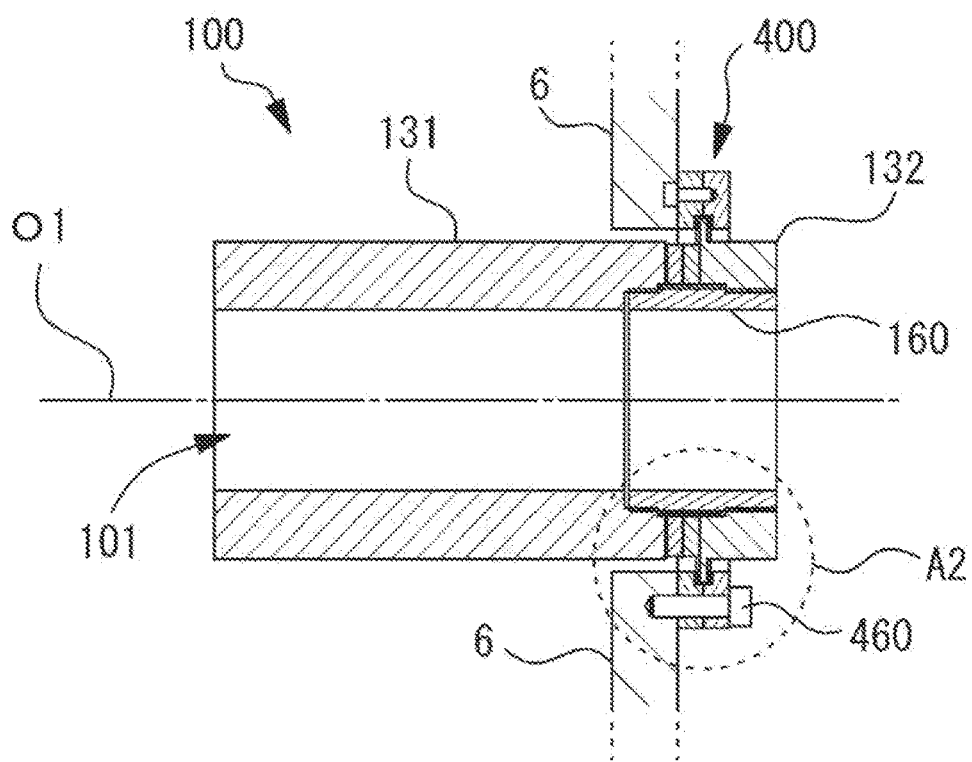
FIG. 5A is a schematic cross-sectional view illustrating an attachment of the example.
Figure 5B:
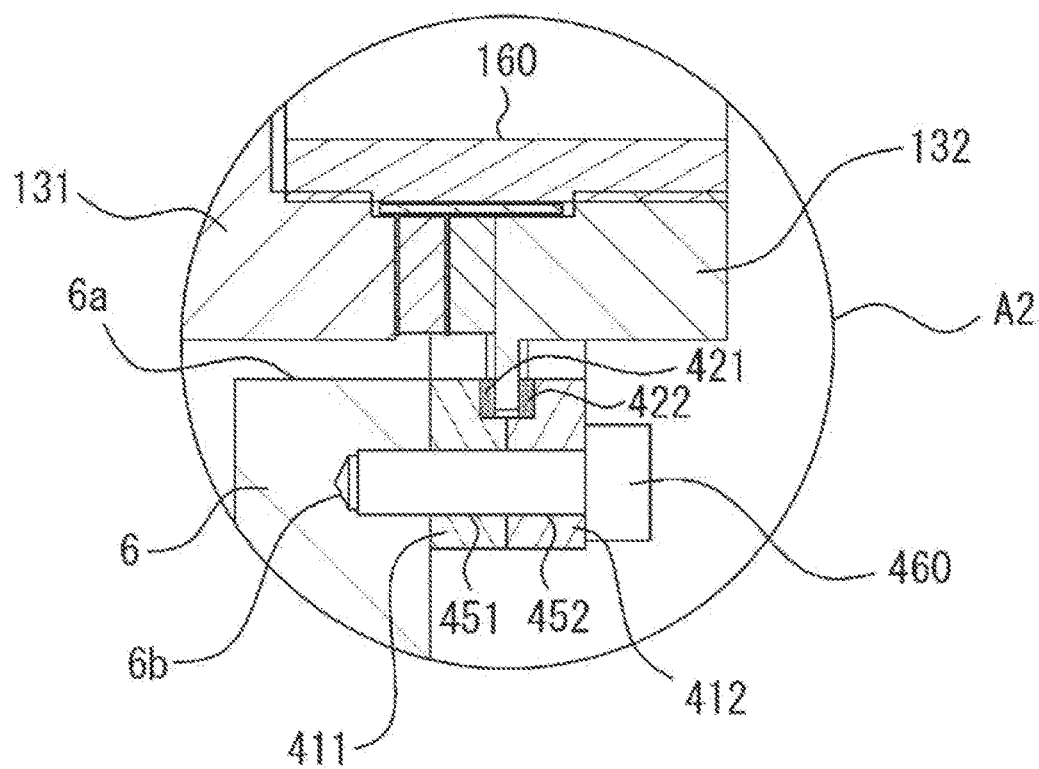
FIG. 5B is a schematic cross-sectional view illustrating the attachment of the example.

FIG. 5A is a cross-sectional view where the ultrasonic unit 100 is attached to the support base 6. FIG. 5B is a state where an area A2 illustrated in FIG. 5A is enlarged. As illustrated in FIGS. 5A and 5B, the first flange 411 and the second flange 412 are fixed to the support base 6; accordingly, the ultrasonic unit 100 is supported by the support base 6. The first flange 411 and the second flange 412 are provided with through-holes 451 and 452 for threading a bolt 460 therethrough. Moreover, a female thread 6b is formed in the support base 6. For example, the bolt 460 is threadedly engaged with the female thread 6b of the support base 6 through the through-holes 451 and 452 of the first flange 411 and the second flange 412 to fix the attachment 400 to the support base 6. Consequently, the ultrasonic unit 100 is attached to the support base 6.

The method for holding the flange 135 by the attachment 400 and the method for fixing the attachment 400 to the support base 6 may not be the method using a bolt. They may be a method using, for example, a screw, a magnet, a hook-and-loop fastener, a vise, a clip, or welding.

The attachment 400 may, for example, be able to adjust the position of the ultrasonic unit 100 with respect to the optical unit 200. For example, the attachment position to the support base 6 may be able to be shifted three-dimensionally. In this case, the attachment 400 functions as an adjuster that adjusts relative positions of the optical unit 200 and the ultrasonic unit 100. For example, the attachment 400 may be configured to fix the ultrasonic unit 100 to the support base 6 in such a manner that the beam axis of the ultrasonic unit 100 is coaxial with the optical axis O1 of the optical unit 200.

Controller

Figure 6:
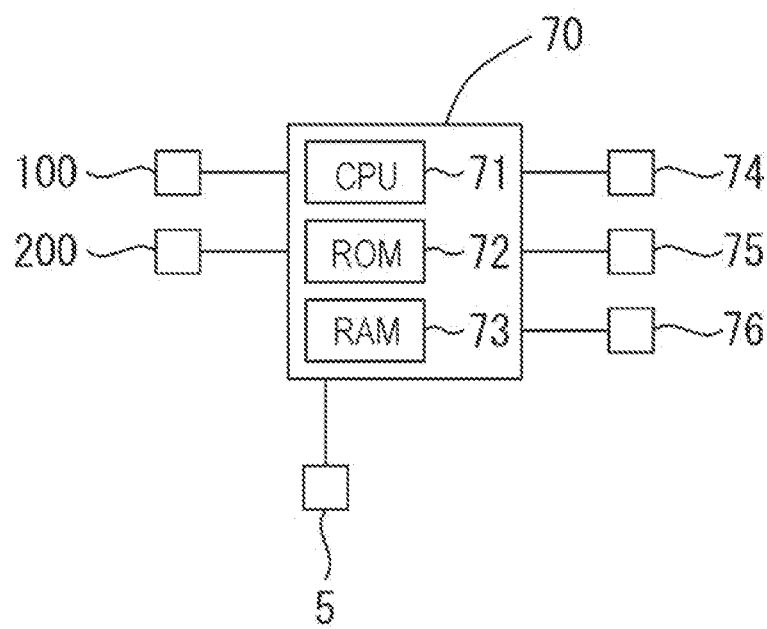
FIG. 6 is a block diagram illustrating a control system of the example.

Next, the configuration of a control system is described, using FIG. 6. A controller 70 performs, for example, control over the entire apparatus, and computational processing on measurement values. The controller 70 is realized by, for example, a general CPU (Central Processing Unit) 71, ROM 72, and RAM 73. Various programs for controlling the operation of the ultrasonic tonometer 1, initial values, and the like are stored in the ROM 72. Various kinds of information are temporarily stored in the RAM 73. The controller 70 may be configured of one controller or a plurality of controllers (that is, a plurality of processors). The controller 70 may be connected to, for example, the driver 5, a storage 74, a display 75, an operating device 76, the ultrasonic unit 100, and the optical unit 200.

The storage 74 is a non-transitory storage medium that can retain stored contents even if the power supply is shut down. For example, a hard disk drive, a flash ROM, or detachable USB memory can be used as the storage 74.

The display 75 displays, for example, a measurement result of the examinee's eye. The display 75 may have a touchscreen function.

The operating device 76 accepts various operation instructions of an examiner. The operating device 76 outputs, to the controller 70, an operation signal in accordance with an inputted operation instruction. The operating device 76 is simply required to use at least any of user interfaces such as a touchscreen, mouse, joystick, and keyboard. If the display 75 is a touchscreen, the display 75 may function as the operating device 76.

Control Operation

The control operation of the apparatus including the above configuration is described. Firstly, the controller 70 aligns the measuring device 3 with the eye of the examinee whose face is being supported by the face supporter 4. For example, the controller 70 detects a bright spot by the target projecting system 250 from an anterior segment front image acquired by the photo detector 222. The controller 70 drives the driver 5 in such a manner as to locate the bright spot in a predetermined location. Naturally, the examiner may perform alignment with the examinee's eye manually by use of, for example, the operating device 76, while viewing the display 75. After driving the driver 5, the controller 70 determines the appropriateness of the alignment on the basis of whether or not the location of the bright spot in the anterior segment image is the predetermined location.

After completing the alignment with the examinee's eye E, the controller 70 measures the corneal thickness by use of the corneal thickness measuring system 270. For example, the controller 70 calculates the corneal thickness on the basis of a light receiving signal received by the photo detector 275. For example, the controller 70 may obtain the corneal thickness from the positional relationship between a peak value by the reflected light from the front surface of the cornea and a peak value of the reflected light from the back surface of the cornea. The controller 70 causes, for example, the storage 74 to store the obtained corneal thickness Next, the controller 70 measures the eye pressure of the examinee's eye by use of the ultrasonic unit 100. For example, the controller 70 applies a voltage to the ultrasonic element, and applies ultrasound to the examinee's eye E. The controller 70 deforms the cornea, for example, by creating acoustic radiation pressure by the ultrasound. The controller 70 then detects the deformed state of the cornea by use of the deformation detecting system 260. For example, the controller 70 detects the deformation of the cornea into a predetermined shape (an applanated state or flattened state) on the basis of a light receiving signal of the photo detector 263.

The controller 70 calculates the eye pressure of the examinee's eye, for example, on the basis of the acoustic radiation pressure of when the cornea of the examinee's eye deforms into the predetermined shape. The acoustic radiation pressure exerted on the examinee's eye is related to ultrasound irradiation time, and increases with increasing ultrasound irradiation time. Therefore, the controller 70 obtains the acoustic radiation pressure of when the cornea deforms into the predetermined shape, on the basis of the ultrasound irradiation time. The relationship between the acoustic radiation pressure of when the cornea deforms into the predetermined shape and the eye pressure of the examinee's eye is previously obtained by, for example, experiment, and stored in, for example, the storage 74. The controller 70 determines the eye pressure of the examinee's eye on the basis of the acoustic radiation pressure of when the cornea deforms into the predetermined shape, and the relationship stored in the storage 74.

Naturally, the eye pressure calculation method is not limited to the above method, and various methods may be used. For example, the controller 70 may obtain eye pressure by causing the deformation detecting system 260 to obtain the amount of deformation of the cornea and multiplying the amount of deformation by a conversion factor. The controller 70 may, for example, correct the calculated eye pressure value in accordance with the corneal thickness stored in the storage 74.

The controller 70 may measure the eye pressure on the basis of the ultrasound reflected by the examinee's eye. For example, the eye pressure may be measured on the basis of a change in the properties of the ultrasound reflected by the examinee's eye. Alternatively, the controller 70 may acquire the amount of deformation of the cornea from the ultrasound reflected by the examinee's eye, and measure the eye pressure on the basis of the amount of deformation.

As in the above example, the Langevin transducer was used as the ultrasonic unit 100 to generate ultrasound. As a result, an output of approximately 165 dB to 172 dB was obtained in an area of a diameter of 3.6 mm.

The ultrasonic tonometer 1 of the example includes the Langevin transducer to cause the cornea of the examinee's eye to deform into the predetermined shape and, accordingly, can measure the eye pressure. Moreover, as in the above example, the ultrasonic unit 100 is provided with the opening 101 and the examinee's eye is observed with the observing system 220 through the opening 101; accordingly, sufficient power ultrasound can be applied to the examinee's eye in a state where the examinee's eye is being observed from the front. Moreover, the examinee's eye can be observed in a direction of the beam axis of ultrasound.

Moreover, as in the above example, the attachment 400 attaches the ultrasonic unit 100 to the support base 6; accordingly, it is possible to reduce an adverse effect such as a reduction in ultrasound output. Furthermore, it is possible to prevent, for example, the vibration of the ultrasonic unit 100 from propagating to other precision portions such as the optical unit 200.

LIST OF REFERENCE SIGNS

1 Non-contact ultrasonic tonometer
2 Base
3 Measuring device
4 Face supporter
6 Support base
100 Ultrasonic unit
200 Optical unit
400 Attachment

The invention claimed is:

1. A non-contact ultrasonic tonometer for measuring the eye pressure of an examinee's eye by use of ultrasound, comprising:
a Langevin transducer including a flange;
a support base supporting the Langevin transducer; and
attaching means for attaching the Langevin transducer to the support base,
wherein the Langevin transducer applies ultrasound to the examinee's eye to measure the eye pressure of the examinee's eye,
the attaching means comprises a first flange, a second flange, a first vibration-isolating member and a second vibration-isolating member, and
the attaching means holds the flange of the Langevin transducer by sandwiching the flange of the Langevin transducer with the first flange and the second flange via the first vibration-isolating member and the second vibration-isolating member.

2. The non-contact ultrasonic tonometer according to claim 1, wherein the Langevin transducer includes a sonotrode, a back mass, and an ultrasonic element sandwiched between the sonotrode and the back mass.

3. The non-contact ultrasonic tonometer according to claim 1, further comprising a fastening member, wherein the Langevin transducer is clamped with the fastening member.

4. The non-contact ultrasonic tonometer according to claim 3, wherein the fastening member is a bolt.

5. The non-contact ultrasonic tonometer according to claim 4, wherein the bolt is a hollow bolt.

6. The non-contact ultrasonic tonometer according to claim 1, wherein the Langevin transducer includes an opening.

7. The non-contact ultrasonic tonometer according to claim 6, further comprising an optical system for measuring or observing the examinee's eye, wherein an optical axis of the optical system is placed in the opening.

8. The non-contact ultrasonic tonometer according to claim 1, wherein the attaching means further comprises a bolt for clamping the first flange and the second flange.

9. The non-contact ultrasonic tonometer according to claim 1, wherein the first vibration-isolating member is placed between the first flange and the flange of the Langevin transducer, and the second vibration-isolating member is placed between the second flange and the flange of the Langevin transducer.

10. A non-contact ultrasonic tonometer for measuring the eye pressure of an examinee's eye by use of ultrasound, comprising:
ultrasonic generating means for generating ultrasound, the ultrasonic generating means including a flange;
a support base supporting the ultrasonic generating means; and
attaching means for attaching the ultrasonic generating means to the support base,
wherein the attaching means comprises a first flange, a second flange, a first vibration-isolating member and a second vibration-isolating member, and
the attaching means holds the flange of the ultrasonic generating means by sandwiching the flange of the ultrasonic generating means with the first flange and the second flange via the first vibration-isolating member and the second vibration-isolating member.

11. The non-contact ultrasonic tonometer according to claim 10, wherein
the ultrasonic generating means is a Langevin transducer including a sonotrode, a back mass, and an ultrasonic element placed between the sonotrode and the back mass, and
the attaching means holds the back mass.

12. The non-contact ultrasonic tonometer according to claim 11, wherein the back mass includes the flange of the ultrasonic generating means.

13. The non-contact ultrasonic tonometer according to claim 11, wherein the attaching means holds the Langevin transducer without contacting the sonotrode.

14. The non-contact ultrasonic tonometer according to claim 11, wherein the support base includes an opening larger than the outer diameter of the sonotrode.

15. The non-contact ultrasonic tonometer according to claim 10, wherein the ultrasonic generating means includes an opening.

16. The non-contact ultrasonic tonometer according to claim 15, further comprising an optical system for measuring or observing the examinee's eye, wherein an optical axis of the optical system is placed in the opening.

17. The non-contact ultrasonic tonometer according to claim 10, wherein the attaching means further comprises a bolt for clamping the first flange and the second flange.

18. The non-contact ultrasonic tonometer according to claim 10, wherein the first vibration-isolating member is placed between the first flange and the flange of the ultrasonic generating means, and the second vibration-isolating member is placed between the second flange and the flange of the ultrasonic generating means.

* * * * *